United States Patent
Shibuya et al.

(10) Patent No.: US 7,223,764 B2
(45) Date of Patent: May 29, 2007

(54) 2,4-BIS (TRIFLUOROETHOXY)PYRIDINE COMPOUND AND DRUG CONTAINING THE COMPOUND

(75) Inventors: Kimiyuki Shibuya, Tokorozawa (JP); Tadaaki Ohgiya, Tokorozawa (JP); Takayuki Matsuda, Higashimurayama (JP); Toru Miura, Higashimurayama (JP)

(73) Assignee: Kowa Co., Ltd., Nagoya-shi (JP)

( * ) Notice: Subject to any disclaimer, the term of this patent is extended or adjusted under 35 U.S.C. 154(b) by 370 days.

(21) Appl. No.: 10/883,710

(22) Filed: Jul. 6, 2004

(65) Prior Publication Data

US 2005/0020606 A1 Jan. 27, 2005

(30) Foreign Application Priority Data

Jul. 7, 2003 (JP) ............... 2003-192853

(51) Int. Cl.
- *A61K 31/496* (2006.01)
- *C07D 213/69* (2006.01)
- *C07D 401/12* (2006.01)
- *C07D 401/14* (2006.01)
- *C07D 403/12* (2006.01)

(52) U.S. Cl. ............... 514/253.09; 544/360; 544/364; 544/370; 546/296

(58) Field of Classification Search ............ 544/364, 544/360, 370; 546/296
See application file for complete search history.

(56) References Cited

U.S. PATENT DOCUMENTS

2004/0176593 A1* 9/2004 Shibuya et al. ............ 540/575
2005/0020606 A1   1/2005 Shibuya et al.

FOREIGN PATENT DOCUMENTS

JP         2004/052861    * 6/2004

WO         WO 98/54153    12/1998

OTHER PUBLICATIONS

Peter J. Gillies, et al., "Regulation of Acyl-CoA: Cholesterol Acyltransferase Activity in Normal and Atherosclerotic Rabbit Aortas: Role of a Cholesterol Substrate Pool", Experimental and Molecular Pathology, vol. 44, 1986, pp. 329-339.
Lei Li, et al., "Effects of high-density lipoprotein$_2$ on cholesterol transport and acyl-coenzyme A:cholesterol acyltransferase activity in P388D1 macrophages", Biochimica et Biophysica Acta, vol. 1530, No. 1, 2001, pp. 111-122.
U.S. Appl. No. 10/498,984, filed Jun. 25, 2004, Shibuya, et al.
U.S. Appl. No. 10/558,197, filed Nov. 25, 2005, Shibuya, et al.

* cited by examiner

*Primary Examiner*—Emily Bernhardt
(74) *Attorney, Agent, or Firm*—Oblon, Spivak, McClelland, Maier & Neustadt, P.C.

(57) ABSTRACT

The present invention is directed to a 2,4-bis(trifluoroethoxy)pyridine compound represented by formula (1):

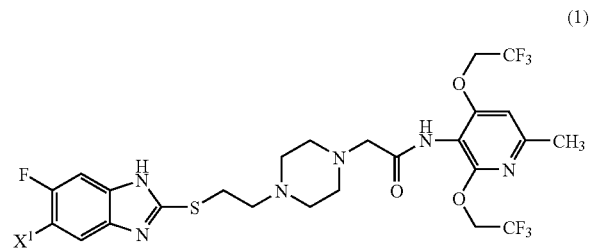

(wherein $X^1$ represents a fluorine atom or a hydrogen atom) or a salt thereof, and to a drug containing the compound or the salt as an active ingredient.

The compound has metabolic resistance in human liver microsome, good absorbability upon oral administration, and excellent ACAT inhibitory activity.

10 Claims, 1 Drawing Sheet

2,4-BIS (TRIFLUOROETHOXY)PYRIDINE COMPOUND AND DRUG CONTAINING THE COMPOUND

BACKGROUND OF THE INVENTION

1. Field of the Invention

The present invention relates to a 2,4-bis(trifluoroethoxy) pyridine compound which exhibits high acyl coenzyme A cholesterol acyltransferase (ACAT) inhibitory effect upon oral administration and thus is useful for prevention or treatment of hyperlipidemia, arteriosclerosis, or similar disorders, and to intermediates which are useful for producing the compound.

2. Description of the Related Art:

Acyl coenzyme A cholesterol acyltransferase (ACAT) is an enzyme which catalyzes the synthesis of cholesterol ester from cholesterol and plays an important role in the metabolism of cholesterol and its absorption in digestive organs. Although many of conventional ACAT inhibitors serving as anti-hyperlipidemia agents or anti-arteriosclerosis agents act on ACAT in the small intestine or the liver to decrease blood cholesterol level, such agents disadvantageously have side effects such as intestinal bleeding, intestinal disorder, diarrhea, and liver disorder.

According to recent studies, regression of arteriosclerosis foci per se is expected to be achieved by preventing foam-cell formation of macrophages, which play a key role in formation of foci of arteriosclerosis. Specifically, macrophage-derived foam cells (which store cholesterol esters therein as fatty droplets) are observed in a focus of arteriosclerosis. It has been revealed that the formation of macrophage-derived foam cells is closely related to the progress of the lesion. In addition, at the arteriosclerosis lesion site, the activity of ACAT on the vascular wall has been elevated, and cholesterol ester has accumulated on the vascular wall. Thus, the activity of ACAT on the vascular wall might have a close relation to arteriosclerosis (Exp. Mol. Pathol., 44, 329–339 (1986)).

Accordingly, when an ACAT inhibitor inhibits esterification of cholesterol on vascular walls, free cholesterol will be stored in vascular wall cells. The stored free cholesterols are removed by high-density lipoprotein (HDL) from the cells to the liver (reverse transport by HDL) and then metabolized. Thus, such an ACAT inhibitor can be expected to inhibit accumulation of cholesterol esters at lesion sites of arteriosclerosis (Biochim. Biophys. Acta. 2001 15, 1530 (1): 111–122). As described above, an ACAT inhibitor which inhibits ACAT present on vascular walls has been considered to have direct anti-arteriosclerosis effect.

Previously, after extensive studies focusing on a prediction that a compound which selectively inhibits ACATs present on vascular walls and thus prevents macrophages from transforming into foam cells may serve as a preventive or therapeutic agent for arteriosclerosis while producing reduced side effects, the present inventors found that a compound represented by the following formula (A):

(A)

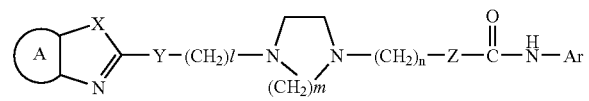

(wherein Ar represents an aryl group which may optionally be substituted,

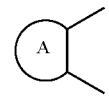

represents a divalent residue of benzene, pyridine, cyclohexane, or naphthalene which may optionally be substituted, X represents NH, an oxygen atom, or a sulfur atom, Y represents a sulfur atom or the like, Z represents a single bond, l is an integer of 0 to 15, m is 2 or 3, and n is an integer of 1 to 3), a salt thereof, or a solvate of the compound or the salt selectively inhibits ACATs present in the artery wall and thus is useful as a preventive or therapeutic agent for hyperlipidemia or arteriosclerosis (International Patent Publication WO98/54153).

Among the compounds described in International Patent Publication WO98/54153, a compound represented by formula (B):

(B)

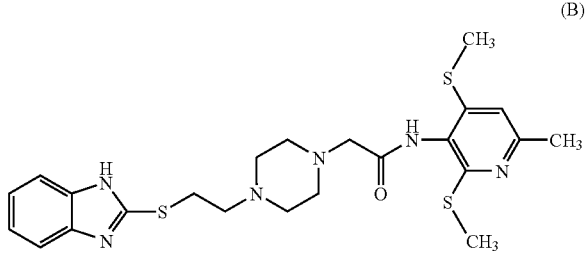

and a salt thereof was found to have high solubility to water and high ACAT inhibitory effect and exhibit unique pharmacological effect in a variety of animal models. Although compound (B) and other compounds disclosed in International Patent Publication WO98/54153 exhibit excellent pharmacological effect attributed to ACAT inhibitory effect in animals, experiments performed in vitro using human liver microsomes revealed that these compounds are rapidly metabolized and thus only small percentage of unchanged compounds remains in human liver microsome. Therefore, low blood concentration of these compounds has become of concern. Moreover, on the basis of a recent knowledge that, from the mechanism of drug interaction, a drug having higher safety is produced from compounds having higher metabolic resistance, a compound having higher metabolic resistance in human liver microsome is desired.

However, it has been considered very difficult to improve stability, against metabolism, of compound (B) while maintaining its ACAT inhibitory effect, since compound (B) has many functional groups which are generally readily metabolized in living organisms, and these functional groups are believed to be essential for production of the pharmacological effect.

SUMMARY OF THE INVENTION

In view of the forgoing, the present inventors have performed extensive studies with an aim to obtain a compound which has improved metabolic resistance in human liver microsome, exhibits good oral absorption, and provides high blood concentration, and unexpectedly have found that a 2,4-bis(trifluoroethoxy)pyridine compound represented by formula (1) shown below has higher blood concentration (Cmax), higher AUC (area under curve of blood concentration-time), and higher oral absorption, although this pyridine compound has lower solubility to water as compared with those of compound (B). In addition, the present inventors have found that these compounds exhibit high ACAT inhibitory activity and thus are useful as a preventive or therapeutic agent for hyperlipidemia or arteriosclerosis. The present invention has been accomplished based on these findings.

Accordingly, the present invention provides a 2,4-bis(trifluoroethoxy)pyridine compound represented by formula (1):

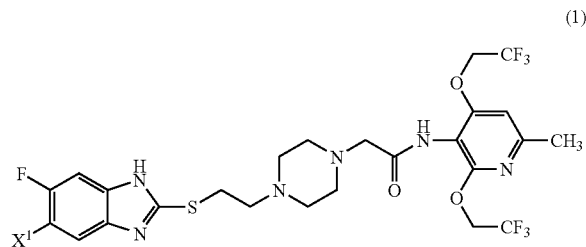

(1)

(wherein $X^1$ represents a fluorine atom or a hydrogen atom) or a salt thereof and a method for producing the compound or the salt.

The present invention also provides a piperazine compound represented by formula (2):

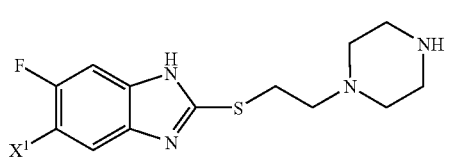

(2)

(wherein $X^1$ represents a hydrogen atom or a fluorine atom) or a salt thereof.

The present invention also provides a pyridine compound represented by formula (4):

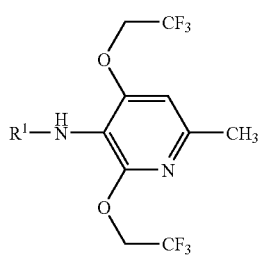

(4)

(wherein $R^1$ represents a hydrogen atom, a chloroacetyl group, a bromoacetyl group, or an iodoacetyl group) or a salt thereof.

The present invention also provides 2,4-bis(2,2,2-trifluoroethoxy)-6-methyl-3-nitropyridine.

The present invention also provides N-[2,4-bis(2,2,2-trifluoroethoxy)-6-methylpyridin-3-yl]-2-[4-(2-hydroxyethyl)piperazin-1-yl]acetamide.

The present invention also provides a drug containing a compound represented by the above formula (1) or a salt thereof as an active ingredient.

The present invention also provides use of a compound represented by the above formula (1) or a salt thereof for producing a drug.

The present invention also provides a method for treating arteriosclerosis, characterized by comprising administering a compound represented by the above formula (1) or a salt thereof in an effective amount.

The compound (1) of the present invention selectively inhibits ACAT present on artery walls, has excellent stability against metabolism in human liver microsome, exhibits good oral absorption, and thus is useful as a preventive or therapeutic agent for hyperlipidemia or arteriosclerosis.

DETAILED DESCRIPTION OF PREFERRED EMBODIMENT(S)

Figure 1:
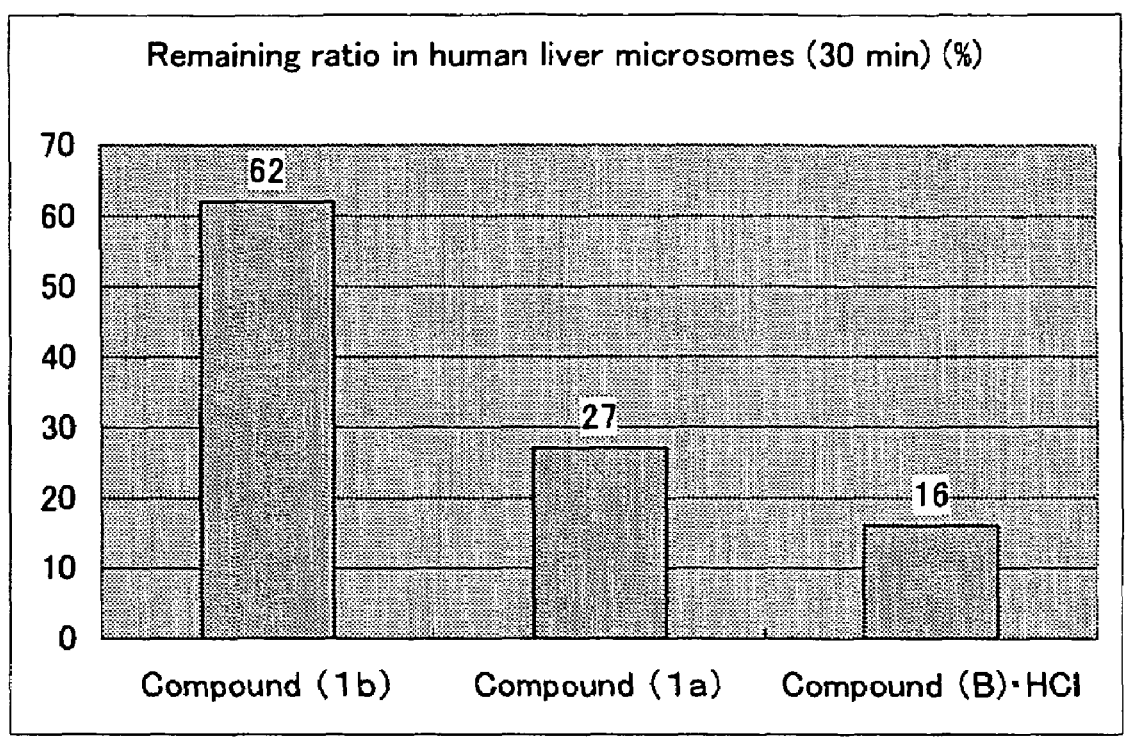
FIG. 1 shows stability against metabolism of compounds (1a), (1b), and compound (B) (hydrochloride) in human liver microsomes.

The compound (1) of the present invention has a structural feature of having one or two fluorine atoms on the benzimidazole ring and having two 2,2,2-trifluoroethoxy groups on the pyridine ring. No compounds having this unique chemical structure has been described in International Patent Publication WO98/54153.

The present invention includes the following two compounds and salts thereof.

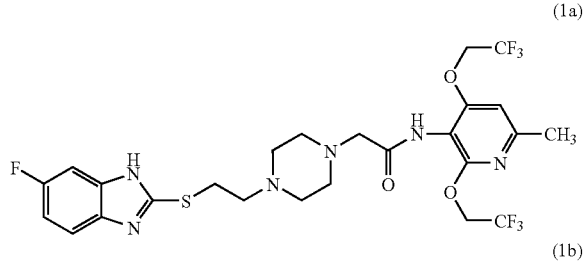

(1a)

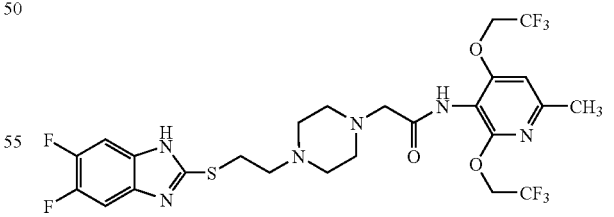

(1b)

Examples of the salt of compound (1) of the present invention include inorganic acid salts such as hydrochlorides, sulfates, nitrates, phosphates; and organic acid salts such as methanesulfonates, maleates, fumarates, citrates, butyrates, lactates, tartrates, ascorbates, malates, mandelates, salicylates, pantothenates, tannates, ethanedisulfonates, benzenesulfonates, p-toluenesulfonates, glutamates, aspartates, trifluoroacetates, pamoates, and gluconates.

The compound (1) of the present invention or a salt thereof may take the form of a solvate. No particular limitation is imposed on the solvate, so far as the solvate does not adversely affect the ACAT inhibitory effect, and the solvate may be formed through addition of a solvent which is employed in the process of production or purification such as water or alcohol. As a solvate, a hydrate is preferred.

The compound (1) of the present invention may be produced through, for example, the following production process.

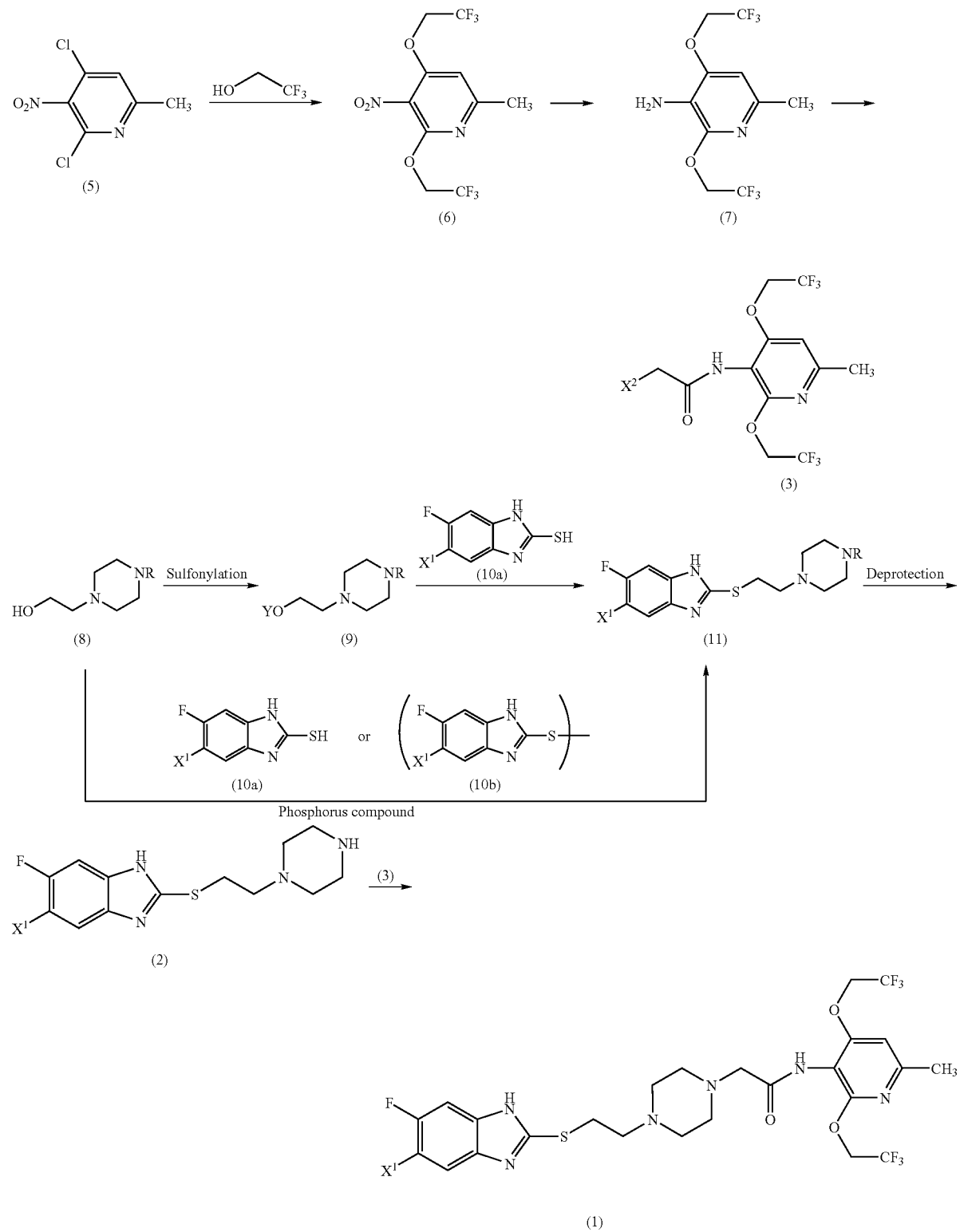

(wherein R represents a protecting group, Y represents a sulfonyl group, $X^1$ represents a hydrogen atom or a fluorine atom, $X^2$ represents a chlorine atom, a bromine atom, or an iodine atom)

Specifically, 2,4-dichloro-6-methyl-3-nitropyridine (5) is reacted with 2,2,2-trifluoroethanol, to thereby produce compound (6). The nitro group of compound (6) is reduced to produce compound (7). Compound (7) is then reacted with halogenoacetic acid or a reactive derivative thereof, to thereby produce compound (3).

Separately, a piperazine ethanol compound (8) whose amino group has been protected is sulfonylated to produce compound (9), and compound (9) is reacted with a thiol derivative (10a) to produce compound (11). Alternatively, compound (11) may be produced through reaction of compound (8) with a thiol derivative (10a) or (10b) in the presence of a phosphorus compound. Compound (2) is produced through deprotection of the protecting group (R) of compound (11).

The compound (1) of the present invention is produced through reaction of the thus-obtained compound (2) with compound (3).

Accordingly, the above compound (2), compound (4) represented by formula (4):

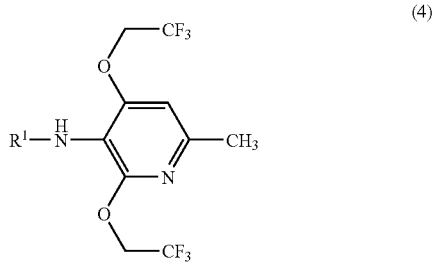

(wherein $R^1$ represents a hydrogen atom, a chloroacetyl group, a bromoacetyl group, or an iodoacetyl group), and the above compound (6) are useful as intermediates for producing the compound (1) of the present invention.

Each step of the above reaction scheme will next be described.

The reaction of 2,4-dichloro-6-methyl-3-nitropyridine (5) with 2,2,2-trifluoroethanol is carried out in a solvent (2,2,2-trifluoroethanol or a solvent mixture thereof with dimethylformamide (DMF), tetrahydrofuran (THF), dimethyl sulfoxide (DMSO), etc.) in the presence of a base (e.g., an alkali metal carbonate such as potassium carbonate or sodium carbonate; an alkali metal hydroxide such as potassium hydroxide or sodium hydroxide; or an alkali metal hydride such as sodium hydride, potassium hydride, or lithium hydride) for 5 to 24 hours at room temperature to reflux temperature (preferably for 15 to 20 hours at reflux temperature).

The reduction of compound (6) is preferably performed through one of the following reduction reactions: (i) reduction through use of a sulfur-containing reduction agent such as sodium dithionite, sodium sulfide, sodium hydrogensulfide, or hydrogen sulfide, (ii) reduction through use of a metal-containing reduction agent such as zinc, iron, or tin (II) chloride, or (iii) catalytic reduction under hydrogen. The reduction reaction (i) is performed by, for example, dissolving compound (6) in a solvent such as isopropanol, ethanol, or THF, adding at 80° C. an aqueous solution of a sulfur-containing reduction agent, and allowing the mixture to react for ten minutes to two hours. The reduction reaction (ii) is carried out by, for example, dissolving compound (6) in a solvent such as an alcohol (such as ethanol or isopropanol), acetic acid, or a mixture solvent of water and any of these solvents and allowing the solution to react for 30 minutes to 24 hours at 0 to 100° C. In the reaction (ii), an acid such as hydrochloric acid or sulfuric acid may be added if necessary. The catalytic reduction reaction (iii) is performed by dissolving compound (6) in a solvent such as dioxane, acetic acid, methanol, ethanol, or isopropanol or a solvent mixture thereof and allowing the solution to react in the presence of a catalyst such as Raney nickel, palladium carbon, palladium hydroxide, or palladium black under hydrogen for 30 minutes to 12 hours at 0 to 50° C., preferably for 30 minutes to three hours at room temperature.

Examples of the halogenoacetic acid to be used in reaction with compound (7) include chloroacetic acid, bromoacetic acid, and iodoacetic acid. Examples of the reactive derivative of the halogenoacetic acid include halogenoacetyl halide and halogenoacetic anhydride. Preferably, compound (7) is reacted with halogenoacetyl halide. The reaction of compound (7) with halogenoacetyl halide is carried out, for example, in a solvent (such as methylene chloride, chloroform, ethyl acetate, acetonitrile, or toluene) in the presence of a base (such as N,N-dimethylaniline, triethylamine, pyridine, 4-dimethylaminopyridine, or 4-pyrrolidinopyridine) for ten minutes to five hours at 0 to 50° C., preferably for 10 to 60 minutes at 0° C.

Synthesis of compound (11) from a piperazine ethanol compound (8) may be performed through Route "a" (through sulfonylation) or Route "b" (through reaction of a phosphorus compound).

In Route "a", sulfonylation of a piperazine ethanol compound (8) is performed in a solvent (such as DMF, THF, ethyl acetate, or acetonitrile) in the presence of a base (such as triethylamine, pyridine, N,N-diisopropylethylamine, N,N-dimethylaniline, or 4-dimethylaminopyridine) through use of a sulfonyl chloride compound, as a sulfonylation agent, such as methanesulfonyl chloride, benzenesulfonyl chloride, or p-toluenesulfonyl chloride for 30 minutes to three hours at 0 to 50° C.

The protecting group (R) of the amino group in piperazine ethanol compound (8) may be protecting groups employed in peptide synthesis. Preferred examples of such protecting groups include alkoxycarbonyl groups (such as benzyloxycarbonyl, 2,2,2-trichloroethyloxycarbonyl, and tert-butoxycarbonyl) and a formyl group.

The reaction of compound (9) with compound (10a) is carried out in a solvent (such as DMF, DMSO, or acetonitrile) in the presence of a base (such as potassium carbonate or sodium carbonate) and a catalyst (such as 18-crown-6) for one to five hours at room temperature to 100° C., preferably for one to two hours at 50 to 80° C.

In Route "b", a piperazine ethanol compound (8) is reacted with a thiol derivative (10a) or (10b) in the presence of a phosphorus compound.

Examples of the phosphorus compound include phosphine reagents employed in Mitsunobu reaction; phosphorous reagents containing such a phosphine reagent and an azo reagent or an ethylenedicarboxylic acid reagent such as dimethyl maleate or N,N,N',N'-tetramethylfumaramide; and phosphonium ylide reagents.

In Route "b", the reaction is preferably performed through any of the following processes: (i) reaction of compound (8) with thiol derivative (10a) in the presence of a phosphine reagent and an azo reagent or an ethylenedicarboxylic acid reagent such as dimethyl maleate or N,N,N',N'-tetramethylfumaramide (Method A), (ii) reaction of compound (8) with a thiol derivative (10a) in the presence of a phosphonium ylide reagent (Method B), and (iii) reaction of compound (8) with a thiol derivative (10b) in the presence of a phosphine reagent (Method C).

<Method A>

Method A may be performed through dissolving compound (8), a thiol derivative (10a), and a phosphine reagent in a reaction solvent, adding an azo reagent or an ethylenedicarboxylic acid reagent thereto, and allowing the mixture to react under argon or nitrogen for 2 to 24 hours at 0° C. to 100° C., preferably at room temperature to 80° C.

Examples of the phosphine reagent employed in Method A include trialkylphosphines such as trimethylphosphine, triethylphosphine, tripropylphosphine, triisopropylphosphine, tributylphosphine, triisobutylphosphine, and tricyclohexylphosphine, and triarylphosphines such as triphenylphosphine, and diphenylphosphinopolystyrene. Among these compounds, trimethylphosphine, tributylphosphine, and triphenylphosphine are preferred.

Examples of the azo reagent include diethyl azodicarboxylate (DEAD), 1,1'-azobis(N,N-dimethylformamide) (TMAD), 1,1'-(azodicarbonyl)dipiperidine (ADDP), 1,1'-azobis(N,N-diisopropylformamide) (TIPA), and 1,6-dimethyl-1,5,7-hexahydro-1,4,6,7-tetrazocin-2,5-dione (DHTD). Among them, diethyl azodicarboxylate is particularly preferred.

Examples of the reaction solvent to be employed include DMF, THF, dioxane, acetonitrile, nitromethane, acetone, ethyl acetate, benzene, chlorobenzene, toluene, chloroform, and methylene chloride. Among them, DMF, THF, dioxane, and acetonitrile are preferred, and DMF and THF are particularly preferred.

<Method B>

Method B may be performed through dissolving compound (8), a thiol derivative (10a), and a phosphonium ylide reagent in a reaction solvent, and allowing the solution to react under argon or nitrogen for 2 to 12 hours at room temperature to 120° C., preferably at 80° C. to 100° C.

Examples of the phosphonium ylide reagent employed in Method B include alkanoylmethylenetrialkylphosphorane, alkanoylmethylenetriarylphosphorane, alkoxycarbonylmethylenetrialkylphosphorane, alkoxycarbonylmethylenetriarylphosphorane, cyanomethylenetrialkylphosphorane, and cyanomethylenetriarylphosphorane. Examples of the trialkyl include trimethyl, triethyl, tripropyl, triisopropyl, tributyl, triisobutyl, and tricyclohexyl. Examples of the triaryl include triphenyl and diphenylpolystyrene.

Alternatively, this reaction may be performed by adding in the reaction solvent, compound (8) and a thiol derivative (10a) with a phosphonium halide reagent in the presence of a base, to thereby produce a phosphonium ylide reagent in the reaction system.

Examples of the phosphonium halide reagent employed in this reaction include (cyanomethyl)trialkylphosphonium halide, (cyanomethyl)triarylphosphonium halide, (alkylcarbonylmethyl)trialkylphosphonium halide, (alkylcarbonylmethyl)triarylphosphonium halide, (alkoxycarbonylmethyl)trialkylphosphonium halide, and (alkoxycarbonylmethyl)triarylphosphonium halide.

Among the above phosphonium halide reagents, (cyanomethyl)trialkylphosphonium halide and (cyanomethyl)triarylphosphonium halide can be prepared through reaction of a corresponding halogenated acetonitrile with a corresponding trialkylphosphine and triarylphosphine, respectively (Tetrahedron, Vol. 57, pp. 5451–5454, 2001). The other reagents can be prepared through reacting a corresponding alkanoylhalomethyl or alkoxycarbonylhalomethyl with a corresponding trialkylphosphine or triarylphosphine in a similar manner.

Examples of the trialkylphosphine and the triarylphosphine include the compounds listed in relation to Method A. Among them, trimethylphosphine, tributylphosphine, and triphenylphosphine are preferred, and trimethylphosphine is particularly preferred.

Examples of the alkanoyl group of the above-described alkanoylhalomethyl include formyl, acetyl, propionyl, and butyryl. Among them, acetyl and propionyl are preferred. Examples of the alkoxy group of the alkoxycarbonylhalomethyl include methoxy, ethoxy, propoxy, and butoxy. Among them, methoxy, ethoxy, and butoxy are preferred.

Preferred examples of the halogen atom include chlorine, bromine, and iodine.

Examples of the base include organic bases such as triethylamine, N,N-diisopropylethylamine, 1,4-diazabicyclo[2,2,2]octane (DABCO), 1,8-diazabicyclo[5,4,0]undeca-7-ene (DBU), and 1,5-diazabicyclo[4,3,0]nona-5-ene (DBN); and inorganic bases such as potassium carbonate, sodium carbonate, cesium carbonate, lithium carbonate, lithium diisopropylamide, and potassium hexamethyldisilazide. Among them, N,N-diisopropylethylamine, potassium carbonate, lithium diisopropylamide, and potassium hexamethyldisilazide are preferred, and N,N-diisopropylethylamine and potassium carbonate are particularly preferred.

Preferred examples of the solvent for reaction include dioxane, THF, toluene, benzene, DMF, DMSO, acetonitrile, and propionitrile, with propionitrile being particularly preferred.

<Method C>

Method C may be performed through dissolving compound (8), a thiol derivative (10b), and a phosphine reagent in a reaction solvent similar to that employed in relation to Method A and allowing reaction of the solution under argon or nitrogen for 2 to 48 hours at room temperature to 100° C., preferably at 60° C. to 100° C.

Examples of the phosphine reagent employed in Method C include trialkylphosphine and triarylphosphine, which are described in relation to Method A. Specific examples include trimethylphosphine, triethylphosphine, tripropylphosphine, triisopropylphosphine, tributylphosphine, triisobutylphosphine, tricyclohexylphosphine, triphenylphosphine, and diphenylphosphinopolystyrene. Among them, trimethylphosphine, tributylphosphine, and triphenylphosphine are preferred, and trimethylphosphine and triphenylphosphine are particularly preferred.

The thiol derivative (10a) may be produced through the method described in the above-mentioned International Patent Publication WO98/54153 or through a method according thereto. The thiol derivative (10b) can easily be produced from the thiol derivative (10a).

The deprotection reaction of compound (11) is performed through a known method in accordance with the protecting group, for example, through hydrolysis, reduction, etc.

The reaction of the thus-obtained compound (2) with compound (3) is carried out in the presence of a base (such as potassium carbonate, sodium carbonate, potassium hydrogencarbonate, or sodium hydrogencarbonate) in a solvent (such as DMF, THF, or acetonitrile, or a mixture solvent of water and any of these solvents), for 5 to 30 hours at room temperature to 50° C., preferably for 10 to 20 hours at room temperature.

Alternatively, the compound (1) of the present invention may be produced through a process of the following reaction scheme:

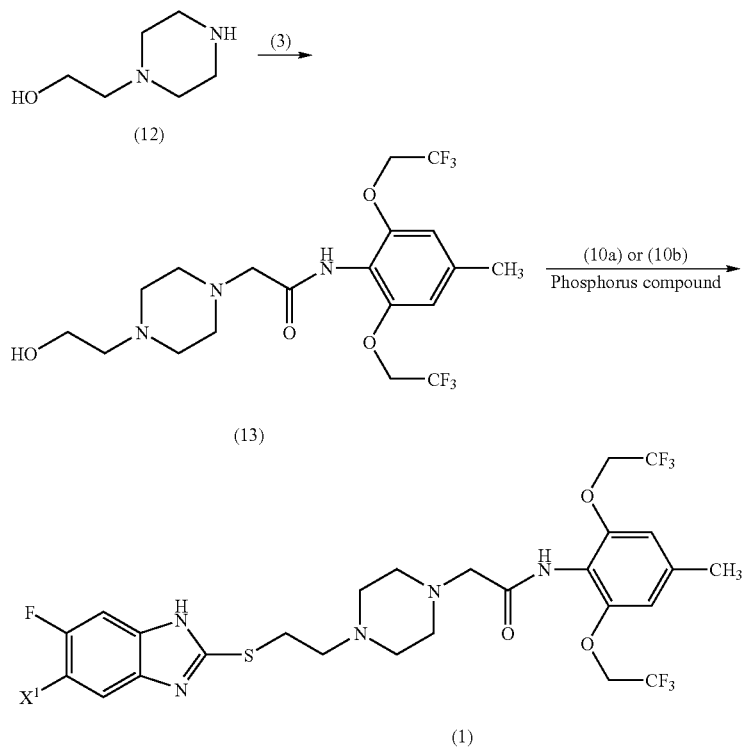

(wherein $X^1$ has the same meaning as defined above). Specifically, 1-(2-hydroethyl)piperazine (12) is reacted with a halogenoacetamide compound (3) to thereby produce compound (13), and compound (13) is reacted with a thiol derivative (10a) or (10b) in the presence of a phosphorus compound.

The reaction of compound (12) with compound (3) is carried out in accordance with a method of producing compound (1) from compound (2).

The reaction of compound (13) with a thiol derivative (10a) or (10b) is carried out in accordance with the reaction of compound (8) with a thiol derivative (10a) or (10b). This indicates that compound (13) is useful as an intermediate in producing compound (1) of the present invention.

Isolation and purification of the compound (1) of the present invention may be performed through any suitable combination of washing, extraction, recrystallization, any types of chromatography, etc. The acid-addition salt may be produced through a routine method.

Resistance to metabolism in human liver microsome was studied in vitro. FIG. 1 shows the residual percentage of the unchanged compound 30 minutes after initiation of reaction. As shown in FIG. 1, compound (B) (hydrochloride) was found to exhibit a residual percentage of 16%, whereas compounds (1a) and (1b) were found to exhibit residual percentages of 27% and 62%, respectively. That is, the compounds of the present invention exhibit higher residual percentage than that of compound (B) (hydrochloride). Therefore, the compound (1) of the present invention was found to have drastically improved metabolic resistance in human liver microsome.

In addition, solubility to water was studied. As shown in Table 3, the solubility to water of compound (1) of the present invention is considerably lower than that of compound (B) (hydrochloride). Thus, the compound (1) of the present invention was anticipated to have low absorbability upon oral administration, which is undesirable.

However, data obtained through an oral administration test in male and female rats have revealed quite different results. Contrary to our expectation, the compound (1) of the present invention was found to exhibit two to three fold blood concentration (Cmax) and two to four fold AUC value as compared with the case where compound (B) (hydrochloride) was employed. Therefore, the compound (1) of the present invention has been acknowledged to have higher oral absorption as compared with compound (B) (hydrochloride).

In addition, ACAT inhibitory activity was studied in vitro. As shown in Table 1, the compound (1) of the present invention was found to exhibit a high ACAT inhibitory activity equivalent to that of compound (B) (hydrochloride).

The above results—the compound (1) of the present invention exhibits high ACAT inhibitory activity comparable to that of compound (B), higher metabolic resistance in human liver microsomes than that of compound (B), and high oral absorption—indicate that the compound (1) of the present invention is useful as a preventive or therapeutic agent for hyperlipidemia or arteriosclerosis The compound (1) of the present invention has an excellent ACAT inhibitory action and thus is useful as an preventive or therapeutic drug for, for example, hyperlipidemia, arteriosclerosis, cervical or cerebral arteriosclerosis, cerebrovascular disorder, ischemic cardiopathy, ischemic enteropathy, coronary arteriosclerosis, nephrosclerosis, arteriosclerotic nephrosclerosis, malignant nephrosclerosis, acute mesenteric vascular occlusion, chronic intestinal angina, ischemic colitis, aortic aneurysm, or arteriosclerosis obliterans (ASO).

When the compound (1) of the present invention is used as a drug, the compound (1) or a salt thereof can be formed, either singly or in combination with one or more pharmacologically acceptable carriers (e.g., an excipient, a binder, and a diluent), into a dosage form such as tablets, capsules, granules, powders, injections, or suppositories. Such a drug preparation can be produced through known methods. For example, a drug preparation for oral administration may be produced by formulating the compound (1) of the present invention with one or more suitable carriers including an excipient such as starch, mannitol, or lactose; a binder such as sodium carboxymethylcellulose or hydroxypropylcellulose: a disintegrant such as crystalline cellulose or calcium carboxymethylcellulose; a lubricant such as talc or magnesium stearate: or a flowability-improving agent such as light anhydrous silicic acid.

The drug of the present invention is administered either orally or parenterally, but oral administration is preferred.

Dose of the drug of the present invention differs depending on, for example, body weight, age, sex, or symptom of the patient. The daily dose of the compound (1) of the present invention for an adult is typically 1 to 500 mg, preferably 5 to 200 mg. The compound (1) is preferably administered once a day or two or three times a day in a divided manner.

EXAMPLES

The present invention will next be described in more detail by way of examples, which should not be construed as limiting the technical scope of the invention.

Production Example 1

Production of 5,6-difluoro-2-mercaptobenzimidazole 4,5-Difluoro-2-nitroaniline (5.75 g, 33.03 mmol) was dissolved in acetic acid (100 mL) and concentrated hydrochloric acid (2.3 mL), and while the mixture was vigorously stirred in an ice bath, zinc powder (6.91 g, 105.6 mmol) was added thereto over ten minutes. The resultant mixture was stirred for 20 minutes at the same temperature and then for 130 minutes at room temperature. Further, zinc powder (1.20 g, 18.35 mmol) was added thereto over five minutes at the same temperature, and the resultant mixture was stirred for 30 minutes at the same temperature. The reaction mixture was concentrated under reduced pressure, and the residue was neutralized with aqueous saturated bicarbonate, followed by filtration through use of Celite. The filtrate was extracted with chloroform, and the organic layer was washed with saturated brine. The product was dried over sodium sulfate anhydrate, and then concentrated under reduced pressure, to thereby yield a brown oil (4.73 g).

The brown oil was dissolved in ethanol (200 mL), and potassium o-ethylxanthate (15.75 g, 98.25 mmol) was added thereto, followed by reflux for 14 hours. The reaction mixture was concentrated under reduced pressure, the residue was extracted with ethyl acetate—1-mol/L hydrochloric acid, and the organic layer was washed with saturated brine. The product was dried over sodium sulfate anhydrate and then concentrated under reduced pressure, and the residue was crystallized from chloroform-hexane, to thereby yield 5,6-difluoro-2-mercaptobenzimidazole (5.58 g, total yield 91%) as a pale brown powder.

Production Example 2

Production of 1-tert-butoxycarbonyl-4-[2-(5,6-difluorobenzimidazol-2-ylthio)ethyl]piperazine To a solution of 1-tert-butoxycarbonyl-4-(2-hydroxyethyl)piperazine (7.40 g, 32.13 mmol) in THF (100 mL), while stirring in an ice-bath, triethylamine (4.36 g, 43.09 mmol), 4-dimethylaminopyridine (200 mg, 1.64 mmol), and methanesulfonyl chloride (7.40 g, 38.76 mmol) were sequentially added. The temperature of the mixture was allowed to room temperature, and the mixture was stirred for 50 minutes. The reaction mixture was filtrated, and the filtrate was concentrated under reduced pressure. The residue was dissolved in DMF (200 mL), and, at room temperature, 5,6-difluoro-2-mercaptobenzimidazole (5.00 g, 26.86 mmol), potassium carbonate (8.64 g, 62.51 mmol), and 18-crown-6 (500 mg, 1.92 mmol) were sequentially added to the solution, followed by stirring for 90 minutes at 80° C. The reaction mixture was concentrated under reduced pressure, and the residue was purified through silica gel column chromatography (silica gel 200 g, hexane: acetone=8:1 to 1:1). The product was crystallized from acetone-ether-hexane, to thereby yield 1-tert-butoxycarbonyl-4-[2-(5,6-difluorobenzimidazol-2-ylthio)ethyl]piperazine (7.26 g, yield 68%) as colorless crystals.

mp: 192.3–193.0° C. IR (KBr): 3061, 2976, 2836, 1672, 1475, 1427(cm$^{-1}$). $^1$H-NMR (400 MHz, CDCl$_3$) δ: 1.50 (9H, s), 2.51–2.68 (4H, m), 2.94 (2H, t, J=5.4 Hz), 3.28 (2H, t, J=5.4 Hz), 3.45–3.65 (4H, m), 6.85–7.62 (2H, m).

Example 1

Production of 1-[2-(5,6-difluorobenzimidazol-2-ylthio)ethyl]piperazine tris(trifluoroacetic acid) salt Under stirring in an ice-bath, 1-tert-butoxycarbonyl-4-[2-(5,6-difluorobenzimidazol-2-ylthio)ethyl]piperazine (7.26 g, 18.22 mmol) was added to trifluoroacetic acid (50 mL) over 15 minutes and dissolved. After the mixture had been stirred for ten minutes under cooling with ice, ether (100 mL) and hexane (100 mL) were added thereto, and the formed crystals were collected through filtration. The crystals were recrystallized from ethanol-ether, to thereby yield 1-[2-(5,6-difluorobenzimidazol-2-ylthio)ethyl]piperazine tris(trifluoroacetic acid) salt (9.58 g, yield 82%) as a pale yellow powder.

mp: 141.2–142.9° C. IR (KBr): 3417, 3026, 2749, 2483, 1671, 1484 (cm$^{-1}$). $^1$H-NMR (400 MHz, DMSO-d$_6$) δ: 2.78–3.26 (10H, m), 3.49 (2H, t, J=7.2 Hz), 7.51 (2H, t, J=9.0 Hz), 8.76 (2H, m)

Production Example 3

Production of 1-[2-(5,6-difluorobenzimidazol-2-ylthio)ethyl]-4-formylpiperazine

1-Formyl-4-(2-hydroxyethyl)piperazine (1.11 g, 7.0 mmol), 5,6-difluoro-2-mercaptobenzimidazole (1.30 g, 7.0 mmol), and diisopropylethylamine (3.62 g, 28.0 mmol) were dissolved in propionitrile (50 mL), and cyanomethyltrimethylphosphonium iodide (6.80 g, 28.0 mmol) was added thereto, followed by stirring for one hour at 92° C. under argon. The reaction mixture was allowed to cool and then poured in water (100 mL), followed by extraction with chloroform (100 mL×3). The organic layer was washed with saturated brine and then dried over sodium sulfate anhydrate, and the product was concentrated under reduced pressure. The crude product was crystallized from acetone-ether, to thereby yield 1-[2-(5,6-difluorobenzimidazol-2-ylthio)ethyl]-4-formylpiperazine (1.78 g, yield 78%) as a yellow crystalline powder.

mp: 197.0–198.0° C. IR (KBr) cm$^{-1}$: 3441, 2825, 1648, 1476, 1431, 1363. $^1$H-NMR (DMSO-d6): δ2.38 (2H, t, J=5.1 Hz), 2.44 (2H, t, J=5.0 Hz), 2.69 (2H, t, J=7.0 Hz), 3.23–3.38 (4H, m), 3.41 (2H, t, J=7.0 Hz), 7.38–7.58 (2H, m), 7.97 (1H, s), 12.8 (1H s). MS (m/z): 326 (M$^+$), 140 (100).

Example 2

Production of 1-[2-(5,6-difluorobenzimidazol-2-ylthio)ethyl]piperazine

1-[2-(5,6-Difluorobenzimidazol-2-ylthio)ethyl]-4-formylpiperazine (1.70 g, 5.2 mmol) was dissolved in methanol (20 mL), and 12N hydrochloric acid (2 mL) was added to the solution, followed by stirring for 18 hours at room temperature. The reaction mixture was concentrated under reduced pressure, and saturated ammonia-methanol was added thereto, followed by stirring for five minutes at room temperature. The solvent was removed under reduced pressure, and the residue was purified through silica gel column chromatography (chloroform: saturated ammonia-methanol=100:3), to thereby yield 1-[2-(5,6-difluorobenzimidazol-2-ylthio)ethyl]piperazine (1.40 g, yield 90%) as a brown oil.

IR (KBr) cm$^{-1}$: 2925, 2853, 1664, 1602, 1478, 1435, 1364. $^1$H-NMR (CDCl$_3$): δ 2.61–2.82 (4H, m), 3.00 (2H, t, J=4.8 Hz), 3.10 (4H, t, J=4.8 Hz), 3.16 (2H, t, J=4.8 Hz), 7.16–7.42 (2H, m). MS (m/z): 298 (M$^+$), 70 (100).

Production Example 4

Production of 2,4-bis(2,2,2-trifluoroethoxy)-6-methyl-3-nitropyridine 2,4-Dichloro-6-methyl-3-nitropyridine (30 g, 144.9 mmol) was dissolved in 2,2,2-trifluoroethanol (250 mL), and potassium carbonate (50 g, 361.8 mmol) was added thereto, followed by reflux for 21 hours. The reaction mixture was diluted with water, and then subjected to extraction with chloroform. The organic layer was washed with saturated brine and then dried over sodium sulfate anhydrate, followed by concentration under reduced pressure, to thereby yield 2,4-bis(2,2,2-trifluoroethoxy)-6-methyl-3-nitropyridine (45.40 g, yield 94%) as a pale yellow solid.

mp: 72.8–73.2° C. IR (KBr) 3432, 3111, 2975, 1610, 1585, 1535 (cm$^{-1}$). $^1$H-NMR (400 MHz, CDCl$_3$) δ: 2.50 (3H, s), 4.49 (2H, q, J=7.7 Hz), 4.85 (2H, q, J=8.3 Hz), 6.53 (1H, s). Elementally Analysis as C$_{10}$H$_8$F$_6$N$_2$O$_4$

| Calculated: | C, 35.94; H, 2.41; N, 8.38 |
| Found: | C, 35.94; H, 2.45; N, 8.49 |

Example 3

Production of 3-amino-2,4-bis(2,2,2-trifluoroethoxy)-6-methylpyridine 2,4-Bis(2,2,2-trifluoroethoxy)-6-methyl-3-nitropyridine (45.00 g, 134.7 mmol) was dissolved in isopropanol (300 mL), and a solution of sodium dithionite (78.00 g, 448.0 mmol) in water (300 mL) was added thereto under stirring at 80° C. Fifteen minutes after starting of the reaction, a solution of sodium dithionite (16.50 g, 94.8 mmol) in water (51 mL) was added to the reaction mixture. Further, 25 minutes after starting of the reaction, a solution of sodium dithionite (11.10 g, 63.8 mmol) in water (51 mL) was added to the reaction mixture and then stirred for ten minutes. After completion of reaction, 4 mol/L aqueous sulfuric acid (201 mL) was added to the reaction mixture, followed by stirring for 30 minutes at 90° C. After the reaction mixture was allowed to cool, 28% aqueous ammonia (360 mL) was added thereto under cooling with ice, followed by stirring for 30 minutes. The reaction mixture was diluted with water and then extracted with chloroform. The organic layer was washed with saturated brine and then dried over sodium sulfate anhydrate, followed by concentration under reduced pressure. The thus-obtained crystals were recrystallized from hexane, to thereby yield 3-amino-2,4-bis(2,2,2-trifluoroethoxy)-6-methylpyridine (32.91 g, yield 80%) as pale yellow needles.

mp: 53.5–53.8° C. IR (KBr): 3453, 3314, 2968, 1603, 1505, 1456 (cm$^{-1}$). $^1$H-NMR (400 MHz, CDCl$_3$) δ: 2.34 (3H, s), 3.66 (2H, br. s), 4.39 (2H, q, J=8.0 Hz), 4.79 (2H, q, J=8.6 Hz), 6.35 (1H, s). Elementary Analysis as C$_{10}$H$_{10}$F$_6$N$_2$O$_2$·0.55H$_2$O:

| Calculated: | C, 38.24; H, 3.56; N, 8.92 |
| Found: | C, 37.96; H, 3.19; N, 8.94 |

Example 4

Production of 2-bromo-N-[2,4-bis(2,2,2-trifluoroethoxy)-6-methylpyridin-3-yl]acetamide N,N-Dimethylaniline (20.46 g, 168.8 mmol) was added to a solution of 3-amino-2,4-bis(2,2,2-trifluoroethoxy)-6-methylpyridine (42.29 g, 139.0 mmol) in dichloromethane (600 mL). While the mixture was stirred under cooling with ice, a solution of bromoacetyl bromide (28.73 g, 142.3 mmol) in dichloromethane (100 mL) was added thereto, followed by stirring for ten minutes. The reaction mixture was diluted with water and then extracted with chloroform. The organic layer was washed with saturated brine and then dried over sodium sulfate anhydrate, followed by concentration under reduced pressure. The thus-obtained crystals were recrystallized from chloroform-hexane, to thereby yield 2-bromo-N-[2,4-bis(2,2,2-trifluoroethoxy)-6-methylpyridin-3-yl]acetamide (50.25 g, yield 85%) as colorless needles.

mp: 152.8–154.0° C. IR (KBr): 3250, 3053, 1677, 1597, 1541, 1456 (cm$^{-1}$). $^1$H-NMR (400 MHz, CDCl$_3$) δ: 2.43 (3H, s), 4.02 (2H, s), 4.42 (2H, q, J=7.9 Hz), 4.78 (2H, q, J=8.5 Hz), 6.47 (1H, s), 7.49 (1H, br s). Elementally analysis as C$_{12}$H$_{11}$BrF$_6$N$_2$O$_3$

| Calculated: | C, 33.90; H, 2.61; N, 6.59 |
| Found: | C, 34.13; H, 2.66; N, 6.65 |

Example 5

Production of 2-[4-[2-(5,6-difluorobenzimidazol-2-ylthio)ethyl]piperazin-1-yl]-N-[2,4-bis(2,2,2-trifluoroethoxy)-6-methylpyridin-3-yl]acetamide (compound 1b)

1-[2-(5,6-Difluorobenzimidazol-2-ylthio)ethyl]piperazine tris(trifluoroacetic acid) salt (4.00 g, 6.25 mmol) and potassium carbonate (31.26 mmol) were dissolved in acetonitrile (100 mL) and water (30 mL). While the solution was stirred under cooling with ice, 2-bromo-N-[2,4-bis(2,2,2-trifluoroethoxy)-6-methylpyridin-3-yl]acetamide (2.20 g, 5.22 mmol) was added thereto over 15 minutes. The temperature of the mixture was allowed to room temperature, and the mixture was stirred for 15 hours. Thereafter, the reaction mixture was diluted with water and then extracted with chloroform. The organic layer was washed with saturated brine and then dried over sodium sulfate anhydrate, followed by concentration under reduced pressure. The residue was purified through silica gel column chromatography (silica gel 150 g, hexane: acetone=4:1 to 2:1 to 1:1). The thus-obtained crystals were recrystallized from chloroform-hexane, to thereby yield 2-[4-[2-(5,6-difluorobenzimidazol-2-ylthio)ethyl]piperazin-1-yl]-N-[2,4-bis(2,2,2-trifluoroethoxy)-6-methylpyridin-3-yl]acetamide (3.04 g, yield 91%) as a pale yellow powder.

mp: 191–192° C. IR (KBr): 3275, 1686, 1604, 1591, 1509 (cm$^{-1}$). $^1$H-NMR (400 MHz, DMSO-d$_6$) δ: 2.38 (3H, s), 2.42–2.62 (8H, m), 2.67 (2H; t, J=6.7 Hz), 3.30 (2H, s), 3.40 (2H, t, J=6.7 Hz), 4.82 (2H, q, J=8.8 Hz), 4.90 (2H, q, J=8.8 Hz), 6.91 (1H, s), 7.47 (2H, m), 8.77 (1H, s), 12.82 (1H, br.s) Elementally Analysis as C$_{25}$H$_{26}$F$_8$N$_6$O$_3$S

| Calculated: | C, 46.73; H, 4.08; N, 13.08 |
| Found: | C, 46.55; H, 4.12; N, 12.94 |

Production Example 5

Production of 5-fluoro-2-mercaptobenzimidazole 4-fluoro-2-nitroaniline (8.00 g, 51.22 mmol) was dissolved in methanol (100 mL), and 10% palladium-carbon powder (0.80 g) was added thereto, followed by stirring for four hours at room temperature under hydrogen atmosphere. The reaction mixture was filtrated, and the filtrate was concentrated under reduced pressure. The residue was purified column chromatography (silica gel 150 g, hexane ethyl acetate=1:4), to thereby yield a brown oil (5.67 g, yield 88%).

The brown oil (5.64 g, 44.72 mmol) was dissolved in ethanol (150 mL), and potassium o-ethylxanthate (8.60 g, 53.65 mmol) was added thereto, followed by reflux for three hours. Potassium o-ethylxanthate (1.43 g, 8.92 mmol) was further added thereto, and the mixture was refluxed for two hours. The reaction mixture was concentrated under reduced pressure, and the residue was purified through column chromatography (silica gel 150 g, hexane:ethyl acetate=2:1), to thereby yield 5-fluoro-2-mercaptobenzimidazole (5.93 g, yield 79%) as a brown powder.

Production Example 6

Production of 1-tert-butoxycarbonyl-4-[2-(5-fluorobenzimidazol-2-ylthio)ethyl]piperazine 1-tert-Butoxycarbonyl-4-(2-hydroxyethyl)piperazine (6.00 g, 26.05 mmol) was dissolved in THF (36 mL), and triethylamine (3.43 g, 33.90 mmol) and 4-dimethylaminopyridine (159 mg, 1.30 mmol) were added thereto. Under cooling with ice, a solution of methanesulfonyl chloride (3.58 g, 31.25 mmol) in THF (9 mL) was added dropwise to the mixture. The resultant mixture was stirred for one hour and then filtrated, and the filtrate was concentrated under reduced pressure. The residue was dissolved in DMF (90 mL). While the solution was stirred at room temperature, 5-fluoro-2-mercaptobenzimidazole (4.82 g, 28.66 mmol), potassium carbonate (5.40 g, 39.07 mmol), and 18-crown-6 (688 mg, 2.60 mmol) were sequentially added to the solution, and the resultant mixture was stirred for two hours at 80° C. The reaction mixture was concentrated under reduced pressure, and water was added to the residue, followed by extraction with ethyl acetate. The organic layer was washed with water and saturated brine, and then dried over sodium sulfate anhydrate, followed by concentration under reduced pressure. The residue was purified through silica gel column chromatography (silica gel 150 g, hexane:ethyl acetate=2:1 to 1:1 to 1:2), to thereby yield 1-tert-butoxycarbonyl-4-[2-(5-fluorobenzimidazol-2-ylthio)ethyl]piperazine (7.28 g, yield 73%).

$^1$H-NMR (400 MHz, CDCl$_3$) δ: 1.49 (9H, s), 2.63 (4H, t, J=4.9 Hz), 2.94 (2H, t, J=5.9 Hz), 3.29 (2H, t, J=5.9 Hz), 3.58 (4H, t, J=4.9 Hz), 6.93 (1H, td, J=9.2, 2.5 Hz), 7.19 (1H, dd, J=9.2, 2.5 Hz), 7.40 (1H, dd, J=9.2, 4.9 Hz).

Example 6

Production of 1-[2-(5-fluorobenzimidazol-2-ylthio) ethyl]piperazine tris(trifluoroacetic acid) salt While trifluoroacetic acid (17 mL) was stirred under cooling with ice, 1-tert-butoxycarbonyl-4-[2-(5-fluorobenzimidazol-2-ylthio)ethyl]piperazine (6.50 g, 17.08 mmol) was added to the acid over 30 minutes and dissolved thereto. The temperature of the mixture was allowed to room temperature, and the mixture was stirred for 30 minutes. Thereafter, ether and hexane were added thereto, and the formed solid was collected through filtration. The collected product was washed with ether, to thereby yield 1-[2-(5-fluorobenzimidazol-2-ylthio)ethyl]piperazine tris(trifluoroacetic acid) salt (10.50 g, yield 99%) as a brown powder.

mp: 127.7–129.3° C. IR (KBr):3143, 3032, 2731, 1789, 1747, 1660 (cm$^{-1}$). $^1$H-NMR (400 MHz, DMSO-d$_6$) δ: 3.29–3.47 (8H, m), 3.48 (2H, t, J=6.6 Hz), 3.62 (2H, t, J=6.6 Hz), 7.03 (1H, t, J=9.0 Hz), 7.32 (1H, d, J=9.0 Hz), 7.48 (1H, dd, J=9.0, 4.4 Hz), 9.36 (2H, br), 13.76 (3H, br).

Production Example 7

Production of 1-[2-(5-fluorobenzimidazol-2-ylthio) ethyl]-4-formylpiperazine

1-Formyl-4-(2-hydroxyethyl)piperazine (1.20 g, 7.6 mmol), 5-fluoro-2-mercaptobenzimidazole (1.28 g, 7.6 mmol), and diisopropylethylamine (3.93 g, 30.4 mmol) was dissolved in propionitrile (50 mL), and cyanomethyltrimethylphosphonium iodide (7.39 g, 30.4 mmol) was added to the mixture, followed by stirring for one hour at 92° C. under argon. The reaction mixture was allowed to cool and then poured into water (100 mL), followed by extraction with chloroform (100 mL×3) The resultant organic layer was washed with saturated brine and then dried over sodium sulfate anhydrate, followed by concentration under reduced pressure. The crude product was crystallized from acetone-ether, to thereby yield 1-[2-(5-fluorobenzimidazol-2-ylthio)ethyl]-4-formylpiperazine (1.87 g, yield 80%) as a brown crystalline powder.

mp: 173.0–175.0° C. IR (KBr) cm$^{-1}$: 3435, 3051, 2953, 2825, 1648, 1503, 1446. $^1$H-NMR (DMSO-d6): δ2.38 (2H, t, J=5.2 Hz), 2.44 (2H, t, J=5.0 Hz)., 2.70 (2H, t, J=7.0 Hz), 3.22–3.38 (4H, m), 3.42 (2H, t, J=7.0 Hz), 6.87–6.98 (1H, m), 7.23 (1H, br s), 7.39 (1H, br s), 7.97 (1H, s), 12.6 (1H s). MS (m/z): 308 (M$^+$), 140 (100).

Example 7

Production of 1-[2-(5-fluorobenzimidazol-2-ylthio)ethyl]piperazine

1-[2-(5-Fluorobenzimidazol-2-ylthio)ethyl]-4-formylpiperazine (1.80 g, 5.8 mmol) was dissolved in methanol (20 mL), 12N hydrochloric acid (2 mL) was added thereto, followed by stirring for 18 hours at room temperature. The reaction mixture was concentrated under reduced pressure, and saturated ammonia-methanol was added thereto, followed by stirring for five minutes at room temperature. The solvent was removed under reduced pressure, and the residue was purified through silica gel column chromatography (chloroform: saturated ammonia-methanol=100:3), to thereby yield 1-[2-(5-fluorobenzimidazol-2-ylthio)ethyl]piperazine (1.33 g, yield 81%) as a brown oil.

IR (KBr) cm$^{-1}$: 3059, 2947, 2815, 1626, 1602, 1482, 1444, 1408. $^1$H-NMR (DMSO-d6): δ 2.30–2.45 (4H, m), 2.62 (2H, t, J=6.8 Hz), 2.67 (4H, t, J=4.8 Hz), 3.39 (2H, t, J=6.8 Hz), 6.90–6.98 (1H, m), 7.23 (1H, dd, J=9.5, 2.5 Hz), 7.39 (1H, dd, J=8.8, 4.9 Hz). MS (m/z): 280 (M$^+$), 70 (100).

Example 8

Production of 2-[4-[2-(5-fluorobenzimidazol-2-ylthio)ethyl]piperazin-1-yl]-N-[2,4-bis(2,2,2-trifluoroethoxy)-6-methylpyridin-3-yl]acetamide (compound 1a)

1-[2-(5-Fluorobenzimidazol-2-ylthio)ethyl]piperazine tris(trifluoroacetic acid) salt (6.92 g, 11.12 mmol) and 2-bromo-N-[2,4-bis(2,2,2-trifluoroethoxy)-6-methylpyridin-3-yl]acetamide (4.50 g, 10.59 mmol) were suspended in acetonitrile (90 mL), and potassium carbonate (5.85 g, 42.33 mmol) was gradually added to the suspension. The mixture was stirred for five hours at room temperature, and water (100 mL) was added to the reaction mixture, followed by extraction with ethyl acetate. The organic layer was washed with saturated brine and then dried over sodium sulfate anhydrate, followed by concentration under reduced pressure. The residue was purified through silica gel column chromatography (chloroform:methanol=50:1). The thus-obtained crystals were recrystallized from acetone-ether, to thereby yield 2-[4-[2-(5-fluorobenzimidazol-2-ylthio)ethyl]piperazin-1-yl]-N-[2,4-bis(2,2,2-trifluoroethoxy)-6-methylpyridin-3-yl]acetamide (4.72 g, yield 71%) as pale brown prisms.

mp: 182.0–182.7° C. IR (KBr): 3282, 2824, 1509, 1413, 1272, 1166 (cm$^{-1}$). $^1$H-NMR (400 MHz, CDCl$_3$) δ: 2.41 (3H, s), 2.66–2.91 (8H, m), 2.97 (2H, t, J=5.1 Hz), 3.25 (2H, t, J=5.1 Hz), 3.29 (2H, s), 4.41 (2H, q, J=8.0 Hz), 4.75 (2H, q, J=8.5 Hz), 6.45 (1H, s), 6.93 (1H, td, J=9.0, 2.3 Hz), 7.10–7.56 (2H, m), 8.28 (1H,s), 13.14 (1H, br.s) Elementary Analysis as C$_{25}$H$_{27}$F$_7$N$_6$O$_3$S:

| Calculated: | C, 48.08; H, 4.36; N, 13.46 |
| Found: | C, 47.98; H, 4.38; N, 13.31 |

Example 9

Production of N-[2,4-bis(2,2,2-trifluoroethoxy)-6-methylpyridin-3-yl]-2-[4-(2-hydroxyethyl)piperazin-1-yl]acetamide 1-(2-hydroxyethyl)piperazin (1.95 g, 15.0 mmol) and 2-bromo-N-[2,4-bis(2,2,2-trifluoroethoxy)-6-methyl-3-pyridin-3-yl]acetamide (5.00 g, 12.5 mmol) were dissolved in acetonitrile (30 ml), and potassium carbonate (2.25 g, 16.3 mmol) was added to the solution. The mixture was stirred for five hours at room temperature, and water was added to the reaction mixture, followed by extraction with ethyl acetate. The organic layer was washed with water and saturated brine and dried over sodium sulfate anhydrate, followed by concentration under reduced pressure. The resultant residue was purified through silica gel column chromatography (developing solvent: ammonia-saturated methanol/chloroform=1/20) to thereby yield N-[2,4-bis(2,2,2-trifluoroethoxy)-6-methylpyridin-3-yl]-2-[4-(2-hydroxyethyl)piperazin-1-yl]acetamide (5.40 g, yield: 91%) as colorless crystals.

$^1$H-NMR (CDCl$_3$) δ: 2.42 (3H, s), 2.48–2.82 (8H, m), 2.57 (2H, t, J=5.3 Hz), 3.17 (2H, s), 3.63 (2H, t, J=5.3 Hz), 4.41 (2H, q, J=8.0 Hz), 4.75 (2H, q, J=8.5 Hz), 6.47 (1H, s), 8.38 (1H, br.s)

Example 10

Production of 2-[4-[2-(5,6-difluorobenzimidazol-2-ylthio)ethyl]piperazin-1-yl]-N-[2,4-bis(2,2,2-trifluoroethoxy)-6-methylpyridin-3-yl]acetamide (compound 1b)

Under argon atmosphere, N-[2,4-bis(2,2,2-trifluoroethoxy)-6-methylpyridin-3-yl]-2-[4-[2-(5,6-difluorobenzimidazol-2-ylthio)ethyl]piperazin-1-yl]acetamide (4.0 g, 8.43 mmol), 5,6-difluoro-2-mercaptobenzimidazole (5.8 g, 31.2 mmol) and triphenylphosphine (7.8 g, 29,7 mmol) were dissolved in N,N-dimethylformamide (170 mL), and under cooling with ice diethyl azodicarbonate (40% w/v toluene solution, 11.0 mL, 25.3 mmol) was added dropwise to the mixture, followed by stirring for 1.5 hours at the same temperature. To the reaction mixture, ethylacetate and 1 mol/L of hydrochloric acid, and aqueous layer was separated. The organic layer was further extracted with 1 mol/L hydrochloric acid. The aqueous layer was combined and the resultant mixture was alkalized by sodium hydroxide (1 mol/L), followed by extraction with ethyl acetate. The organic layer was washed with water and saturated brine and then dried over sodium sulfate anhydrate, followed by concentration under reduced pressure. The residue was purified through silica gel column chromatography (developing solvent; chloroform ammonia-saturated methanol=100:3), to thereby yield 2-[4-[2-(5,6-difluorobenzimidazol-2-ylthio)ethyl]piperazin-1-yl]-N-[2,4-bis(2,2,2-trifluoroethoxy)-6-methylpyridin-3-yl]acetamide (4.9 g, yield: 90.1%) as colorless crystals.

Test Example 1

Test for ACAT Inhibitory Activity in J774A Cells

J774 cells ($2 \times 10^5$ cells/well) were seeded on a 24-well plate and incubated for 24 hours in DMEM (10% FBS, 500 μL). After replacement with a new medium, 25-hydroxycholesterol (10 μg/mL) and ACAT inhibitor (final concentration: 0, $10^{-9}$ to $10^{-5}$ mol/L) were added thereto, followed by incubation for 18 hours. After washing with 0.9% sodium chloride, the lipid was extracted with hexane-isopropanol (3:2) (250 μL) and then with hexane-isopropanol (3:2) (250 μL) again. The extracts were combined, and the solvent was removed. The thus-obtained cholesterol ester (CE) was quantified through the fluorescent enzyme assay. The cells from which the lipid had been extracted were subjected to protein assay (micro BCA assay), to thereby determine the amount of CE per mg of protein. From a CE production ratio of the test compound with respect to that of the control, $IC_{50}$ (concentration of the compound inhibiting 50% of CE production) was calculated at N=4.

The results are shown in Table 1. As shown in Table 1, the compounds (1a) and (1b) were confirmed to have high ACAT inhibitory activity.

TABLE 1

|  | ACAT inhibitory activity: J774A cells: $IC_{50}$ (nM) |
|---|---|
| Compound (1a) | 87 |
| Compound (1b) | 75 |
| Compound (B).HCl | 59 |

Test Example 2

Test on Stability Against Metabolism in Human Liver Microsome

In accordance with Table 2 described below, an NRS (NADPH regenerating system) solution and 16% human serum albumin were added to 0.1 mol/L phosphate buffer (pH 7.4), and a solution of a test compound (100 μM) in acetonitrile (0.01 mL) was added thereto. The mixture was pre-incubated for five minutes in a warm bath at 37° C., and human liver microsome (POOLED HUMAN LIVER MICROSOMES, Lot. No. 20, product of GENTEST) was added thereto, followed by allowing reaction for 30 minutes in a warm bath at 37° C. An aliquot (0.25 mL) was collected from the reaction mixture 0 and 30 minutes after the start of reaction, followed by extraction*. The amount of the test compound was determined through HPLC. Residual percentage of the unchanged compound after 30 minutes was calculated based on the following equation: peak area after 30 minutes/peak area at 0 minute)×100.

The results are shown in FIG. 1. As is shown in FIG. 1, compounds (1a) and (1b) were confirmed to have drastically improved metabolic resistance in human liver microsome as compared with compound (B) (hydrochloride).

TABLE 2

| Composition of the reaction mixture of Human liver microsome (1 mL) | |
|---|---|
| Human liver microsome (POOLED): containing 1 mg of protein in 0.05 mL | 0.05 mL |
| NRS(NADPH regenerating system) solution: containing, in 0.25 mL thereof, 2 mg of β-nicotinamide-adenine dinuleotide, oxidized form type, 2 mg of D-glucose 6-phosphate disodium, and 0.8 unit of glucose 6-phosphate dehydrogenase | 0.25 mL |
| 16% Human serum albumin | 0.25 mL |
| 0.1 mol/L Phosphate buffer (pH 7.4) | 0.44 mL |
| Acetonitrile solution of test compound (100 μM) | 0.01 mL |
| Total | 1 mL |

*Extraction Procedure

To each sample, gkycine buffer (pH 10, 1.0 mL), an internal standard substance (0.1 mL), and tert-butyl methyl ether (5.0 mL) were added. The mixture was shaken for ten minutes and then centrifuged at 2,500 rpm for minutes, and the orginal layer was collected.

Test Example 3

Solubility Test (Japanese Pharmacopoeia Solution I)

Each test compound was dissolved in acetonitrile to form a 100 μM solution, and the solution was added to Japanese Pharmacopoeia Solution I to form a 1000 ng/mL solution. The resultant solution was stirred for ten minutes, and an aliquot (1 mL) was placed into an injection tube and then passed through a 0.2-μm filter (HLC-DISK 13, water/solvent, Kanto Kagaku Kabushiki-kaisya). The filtrate (0.5 mL) was subjected to the extraction procedure*, and the amount of the test compound was determined through HPLC.

The results are shown in Table 3. As shown in Table 3, compound (1a) and compound (1b) were found to have a lower solubility as compared with that of compound (B) (hydrochloride). Therefore, the compounds of the present invention were expected to have low absorbability upon oral administration based on the solubility test results.

TABLE 3

|  | Solubility: Japanese Pharmacopoeia solution I (pH 1.2) (ng/mL) |
|---|---|
| Compound (1a) | 562 |
| Compound (1b) | 422 |
| Compound (B).HCl | 12,500,000 |

*Extraction Procedure

The extraction was performed in a manner similar to that of the test on stability against metabolism in human liver microsome.

Test Example 4

Oral Administration Test in Rats

Each test compound was dissolved in a 0.01N hydrochloric acid solution, and the solution was perorally administered to male or female rats at 10 mg/5 mL/kg. Blood samples (0.25 mL each) were collected 30, 60, 120, 180, 240, and 360 minutes after administration. The collected blood samples were centrifuged for five minutes at 4° C. and 9,000 g, to thereby prepare plasma samples. The plasma samples were stored at −30° C. before measurement. The samples were subjected to the extraction procedure*, and plasma levels of the test compound were determined through LC/MS/MS. The results are shown in Table 4. As shown in Table 4, compound (1a) and compound (1b) were found to exhibit higher Cmax and higher AUC (area under curve) as compared with compound (B) (hydrochloride), confirming that compound (1a) and compound (1b) have good absorbability upon oral administration as compared with compound (B) (hydrochloride).

TABLE 4

| | Cmax (ng/mL) | | AUC (µg · min/mL) | |
|---|---|---|---|---|
| | Male rat | Female rat | Male rat | Female rat |
| Compound (1a) | 418 | 3411 | 22 | 306 |
| Compound (1b) | 614 | 2836 | 55 | 393 |
| Compound (B).HCl | 207 | 1167 | 12 | 148 |

(10 mg/kg · p.o.)

*Extraction Procedure

The extraction was performed in a manner similar to that of the test on stability against metabolism in human liver microsome.

As compared with the compound (B) described in International Patent Publication WO98/54153, the compound (1) of the present invention was found to exhibit excellent stability against metabolism in human liver microsome and high ACAT inhibitory activity. Although the compound (1) of the present invention has lower solubility to water as compared with compound (B) (hydrochloride), it exhibits good oral absorption as indicated in the oral administration test in rats. Therefore, the compound (1) of the present invention is expected to have excellent bioavailability in humans.

What is claimed is:

1. A 2,4-bis(trifluoroethoxy)pyridine compound represented by formula (1):

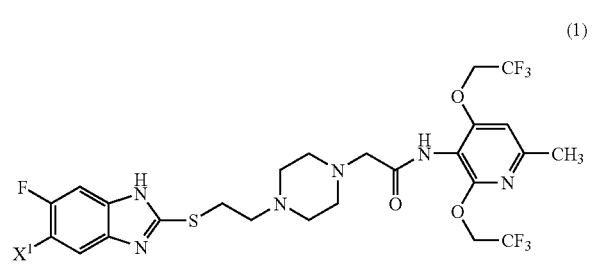

(1)

(wherein $X^1$ represents a fluorine atom or a hydrogen atom) or a salt thereof.

2. A method for producing a compound or a salt thereof as recited in claim 1, comprising reacting a piperazine compound represented by formula (2):

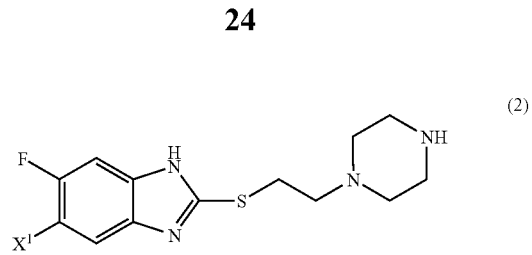

(2)

(wherein $X^1$ represents a fluorine atom or a hydrogen atom) with a pyridine compound represented by formula (3):

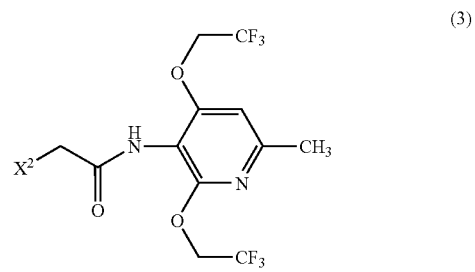

(3)

(wherein $X^2$ represents a chlorine atom, a bromine atom, or a iodine atom).

3. A piperazine compound represented by formula (2):

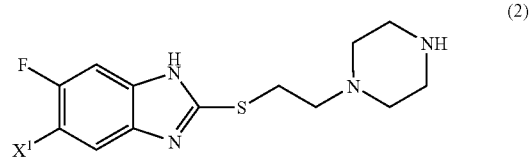

(2)

(wherein $X^1$ represents a fluorine atom or a hydrogen atom) or a salt thereof.

4. A pyridine compound represented by formula (4):

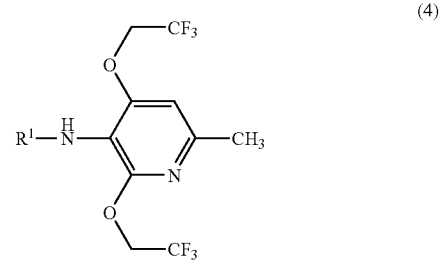

(4)

(wherein $R^1$ represents a hydrogen atom, a chloroacetyl group, a bromoacetyl group, or an iodoacetyl group) or a salt thereof.

5. 2,4-Bis(2,2,2-trifluoroethoxy)-6-methyl-3-nitropyridine.

6. N-[2,4-bis(2,2,2-trifluoroethoxy)-6-methylpyridin-3-yl]-2-[4-(2-hydroxyethyl)piperazin-1-yl]acetamide.

7. A drug composition comprising a compound or a salt thereof as recited in claim 1 and a pharmacologically acceptable carrier therefor.

8. A method for treating hyperlipidemia and/or arteriosclerosis, comprising administering a compound or a salt thereof as recited in claim 1.

9. The compound according to claim 1, which is 2-[4-[2-(5,6-difluorobenzimidazol-2-ylthio)ethyl]piperazin-1-yl]-N-[2,4-bis(2,2,2-trifluoroethoxy)-6-methylpyridin-3-yl]acetamide.

10. The compound according to claim 1, which is 2-[4-[2-(5-fluorobenzimidazol-2-ylthio)ethyl]piperazin-1-yl]-N-[2,4-bis(2,2,2-trifluoroethoxy)-6-methylpyridin-3-yl]acetamide.

* * * * *